United States Patent [19]

Burnett

[11] Patent Number: 4,559,649
[45] Date of Patent: Dec. 24, 1985

[54] URINE SPECIMEN COLLECTION SYSTEM
[75] Inventor: Patricia A. Burnett, Placentia, Calif.
[73] Assignee: Panett Corporation, La Habra, Calif.
[21] Appl. No.: 497,686
[22] Filed: May 24, 1983
[51] Int. Cl.$^4$ .................................................. A47K 11/00
[52] U.S. Cl. ......................................... 4/144.1; 4/144.2; 4/144.4
[58] Field of Search .................... 4/144.1, 144.2, 144.3, 4/144.4

[56] References Cited

U.S. PATENT DOCUMENTS

| | | | |
|---|---|---|---|
| 3,082,434 | 3/1963 | Greene | 4/144.1 |
| 3,161,891 | 12/1964 | Bauman | 4/144.1 |
| 3,781,922 | 1/1974 | Ericson | 4/144.1 |
| 3,811,136 | 5/1974 | Whitney et al. | 4/144.1 |
| 3,832,738 | 9/1974 | Kliemann | 4/144.1 X |
| 3,878,571 | 4/1975 | Seeley | 4/144.1 |
| 3,881,465 | 5/1975 | Raitto | 4/144.1 X |

Primary Examiner—Henry K. Artis
Attorney, Agent, or Firm—Albert L. Gabriel

[57] ABSTRACT

A urine specimen collection system wherein a collection funnel and attached collection lid are first releasably connected to a specimen cup by structure of a first peripheral connection between the collection lid and the cup; and then after a urine specimen has been collected this first connection is released and a storage lid is releasably connected to the cup by structure of a second peripheral connection. The first connection is more easily releasable than the second one, and need not be water-tight; while the second connection is more secure and is preferably substantially water-tight for transport and storage of a collected specimen.

11 Claims, 11 Drawing Figures

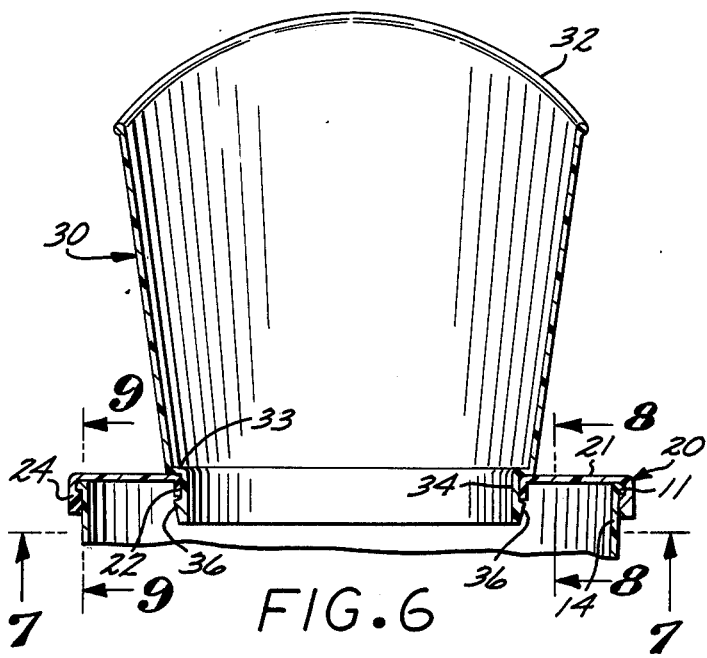
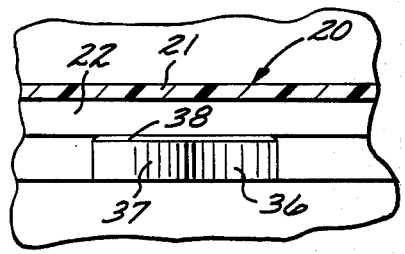
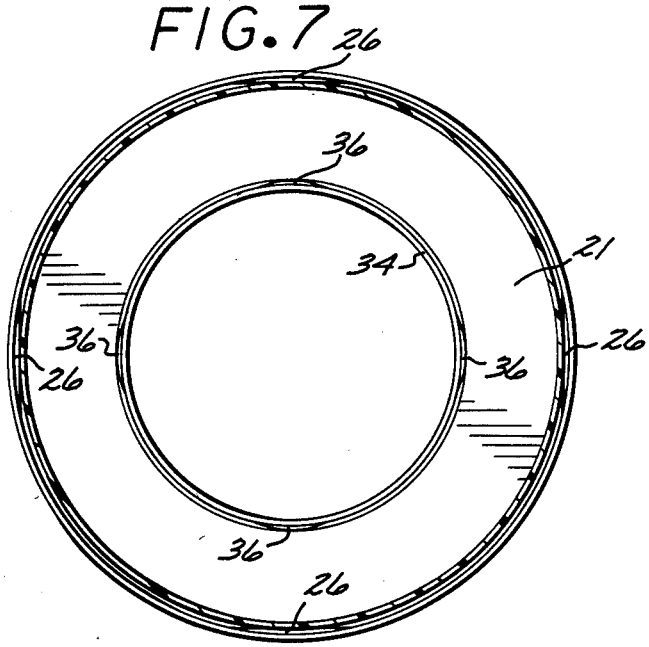
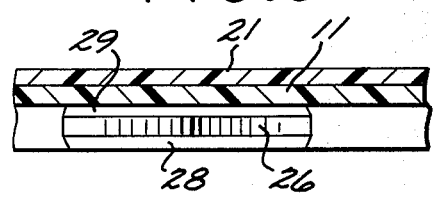
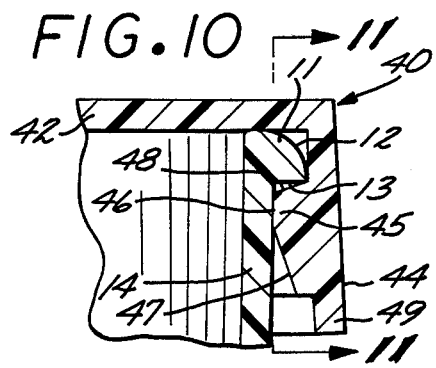
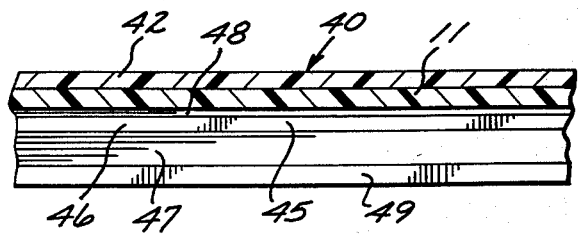

URINE SPECIMEN COLLECTION SYSTEM

BACKGROUND OF THE INVENTION

1. Field of the Invention

The invention is in the field of urine sample collection methods and devices.

2. Description of the Prior Art

For the collection of urine specimens for urinalysis the conventional prior art procedure is to ask a patient, or other subject, to urinate into a cup-like container while standing or sitting. The container may be either disposable or reusable and may or may not have an associated lid. This procedure, especially for females, can prove awkward, messy, and thus unsanitary. Improper sterilization of a reusable container by the laboratory can result in the transmission of infectious or virulent particles onto the user's skin and genitalia. Use of a cup without an associated lid or with a lid that does not form a proper seal creates difficulties in storing and transporting the sample until urinalysis is convenient.

Attempts to improve the efficiency and sanitation of this procedure have fallen generally into two categories; the development of various generally funnel-shaped devices and the development of funnel or tube-shaped devices associated with a container. Examples of funnel-shaped devices are disclosed in U.S. Pat. No. 3,964,111; and in U.S. Pat. Nos. Des. 158,693; Des. 178,749; Des. 195,930; Des. 208,609; and Des. 249,997. These devices do not address the problem of storing a urine specimen.

Examples of funnel-shaped devices in conjunction with urine specimen containers are disclosed in U.S. Pat. Nos. 3,171,136; 3,473,172; 3,625,654; 3,703,731; and in U.S. Pat. Nos. Des. 138,651; Des. 212,792; and Des. 227,413. In U.S. Pat. No. 3,171,136 and U.S. Pat. Nos. Des. 212,792 and Des. 227,413 the specimen container is implied only by any of various provisions for coupling such a container with a generally funnel-shaped device.

The above-referenced U.S. Pat. No. 3,625,654 discloses a funnel that is sealed at its spout end forming another sort of cup with the same essential difficulties as the conventional art.

In U.S. Pat. No. Des. 138,651 a funnel is used in conjunction with a compatible container. There is no provision for replacing the funnel with a lid of any sort or indeed for disengaging the funnel.

Other related implements which bear some limited resemblance to the present invention include a portable urinal with a pivoting retractable hose connection disclosed in U.S. Pat. No. 3,703,731. A female urinal for use by bedridden patients is disclosed in U.S. Pat. No. 3,473,172. The funnel-like device in this apparatus is attached to a boxlike container by either a bayonet or a tapering nozzle-like connection.

None of these prior art devices provide a suitable system for the collection and storage of urine specimens, and in particular, none of these prior art devices discloses or suggests the separately defined connection and storage states of the present invention.

SUMMARY OF THE INVENTION

In view of these and other problems in the art, it is the general object of the present invention to provide a compact urine specimen collection system efficiently incorporating means of collecting and storing a urine specimen from either a male or female subject.

Another object of the present invention is to provide a urine speciman collection system with a funnel assembly in order to aid a subject in filling an incorporated specimen cup with a specimen for urinalysis.

Another object of the present invention is to provide a specimen cup compatible with both a funnel assembly and a storage lid.

A further object is to provide a specimen cup of the character described which engages and disengages relatively easily from a funnel assembly and yet effectively seals when a storage lid is snapped over the mouth.

A still further object is to provide a urine specimen collection system of the character described above molded entirely of an inexpensive plastic material that will eliminate sterilization problems by making the system disposable.

Yet another object of the present invention is to provide a urine specimen collection system that, when unassembled, is stackable and hence storage-efficient in its separate parts.

The specimen cup of the present invention has a lip capable of engaging an annular collection lid by snapping past regularly spaced latching rib segments on the inside of the collection lid. A funnel, also with latching rib segments regularly spaced about the circumference of its spout end, is snapped into the opening in the annular top. In this state the urine specimen is collected. The funnel has a saddle-shaped mouth that fits comfortably between the user's legs close to the body. It is therefore a simple task to access and fill the specimen cup.

Once the specimen has been collected, the funnel and collection lid are easily removable as a unit due to the fact that the connection between funnel and collection lid is much more secure than that between the collection lid and specimen cup. Thus an upward force on the funnel will disengage the collection lid from the specimen cup. The funnel and collection lid, like the rest of the system, are molded from inexpensive plastic material rendering them immediately disposable.

The specimen, having been retained in the specimen cup, is stored for future urinalysis by sealing the specimen cup with a storage lid. This storage lid has a full annular ridge on its inside edge capable of interlocking with the cup lip. The annular ridge is to be contrasted with the rib segments on the funnel and collection lid in that it provides, in conjunction with the lip of the specimen cup, a more secure connection between storage lid and cup than is to be found anywhere else in the system. Whereas the interrupted connection between the rib segments of the collection lid and the specimen cup lip lends itself to efficient engagement and disengagement, the seal between specimen cup and storage lid allows for the long-term, water-tight, storage of the specimen.

BRIEF DESCRIPTION OF THE DRAWINGS

These and other objects of the invention will become more apparent in view of the following description taken in conjunction with the drawings, wherein:

FIG. 6 is a vertical section taken along line 6—6 in FIG. 3;

FIG. 7 is a horizontal section taken along line 7—7 in FIG. 6;

FIG. 8 is a greatly enlarged fragmentary section taken along line 8—8 in FIG. 6;

FIG. 9 is a greatly enlarged fragmentary section taken along line 9—9 in FIG. 6;

FIG. 10 is a greatly enlarged fragmentary vertical section taken along the line 10—10 in FIG. 2; and FIG. 11 is a greatly enlarged fragmentary section taken along line 11—11 in FIG. 10.

DETAILED DESCRIPTION

Figure 1:
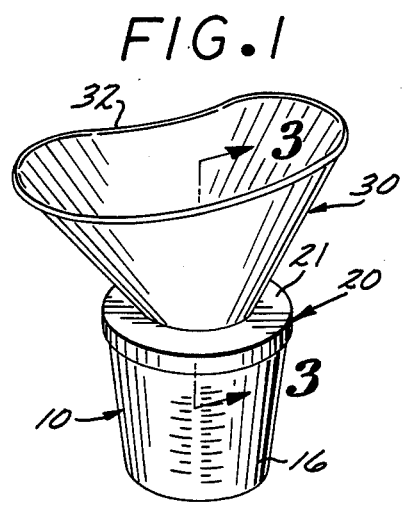
FIG. 1 is a perspective view showing a urine specimen collection system according to the invention in its collection state.
Figure 2:
FIG. 2 is a perspective view showing a urine specimen collection system according to the invention in its storage state.
Figure 3:
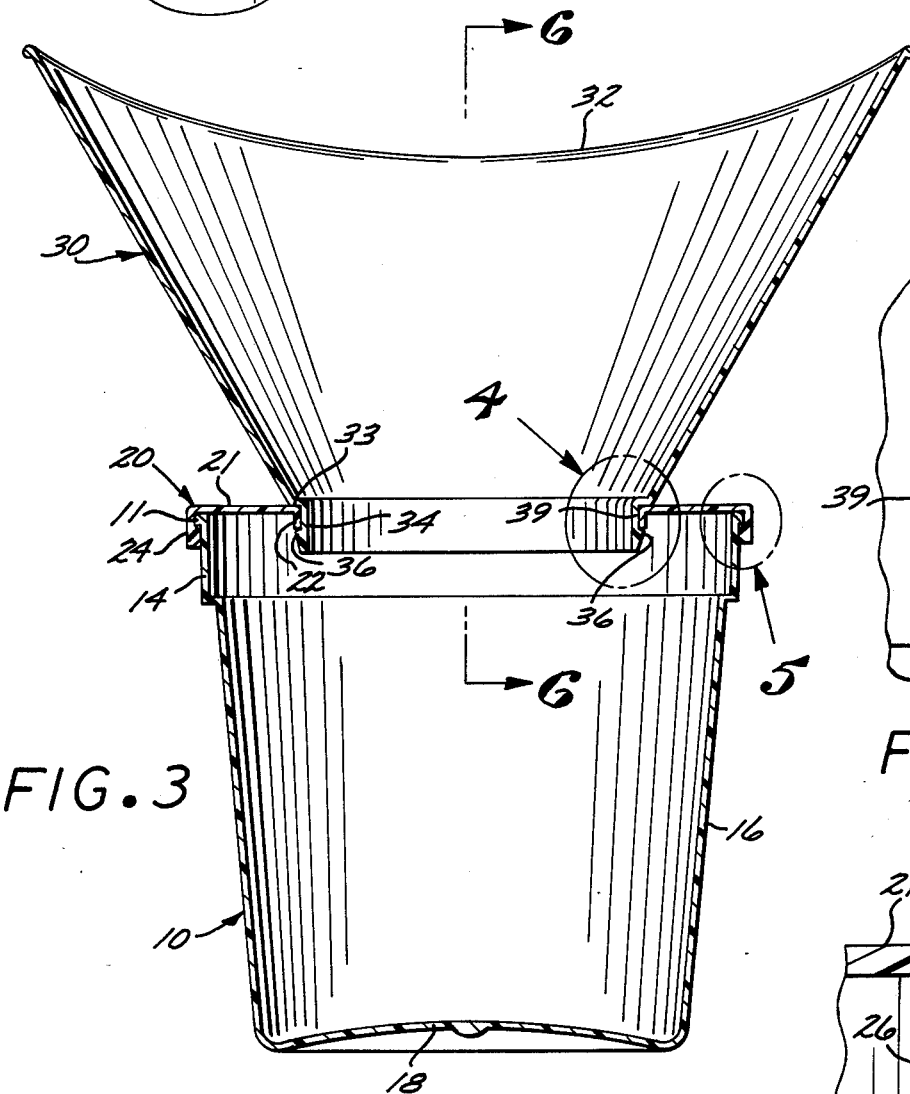
FIG. 3 is a vertical section taken along the lengthwise plane of symmetry (from one end to the other of the saddle-shaped funnel mouth) of the invention in its collection state.

Referring to the drawings, and at first particularly to FIGS. 1 to 3 thereof, the preferably graduated specimen cup of the present invention is generally designated 10, having a cup wall 16 that encloses a cup interior of uniformly increasing cross-sectional diameter from the cup base 18 to the join of cup wall 16 with a cylindrical mouth segment 14. Into this cup a urine specimen is collected and then stored for future urinalysis.

The cylindrical mouth segment 14 of the specimen cup 10 has an outwardly protruding annular lip 11 suitable for interlocking with two different lids as required by the invention in its two utilitarian states. The annular lip 11 has an upwardly facing rounded shoulder 12 and a flat downwardly facing engaging surface 13 extending from the cylindrical mouth segment at an angle of approximately 90°.

Here, as elsewhere in these descriptions, vertical dimensions (top, base, upward, downward) refer to a static model of the invention in its storage orientation and are not meant to limit the functionality of the invention in its collection state. Centrical dimensions (inner, inward, outer, outward) refer to the axis of symmetry of the specimen cup 10 as central.

In the collection state of the present invention, a collection lid 20 is snapped onto the mouth of the specimen cup (FIGS. 3, 5, 6, 9). The top 21 of the collection lid 20 is in the shape of an annulus (FIG. 7) having cylindrical downwardly projecting edge extensions 22 and 24 on its respective inner and outer concentric perimeters. As best seen in FIGS. 7 and 9, the outer cylindrical downwardly projecting edge extension 24 has preferably four regularly circumferentially spaced, inwardly projecting chordal rib segments 26 capable of interlocking with the annular lip 11 of the specimen cup 10. The chordal rib segments 26 are chamfered on both top and bottom forming a downwardly facing entry ramp 28, to facilitate snapping the collection lid 20 into place, and an upwardly facing release ramp 29, to facilitate removal of the lid 20 after use. The release ramp 29 is of a relatively gentle chamfer (preferably approximately 45°) so that the connection between cup 10 and collection lid 20 is relatively easily broken to facilitate the removal of the funnel 30 and collection lid 20, together as a unit so that they may be replaced by the storage lid described below. The join of the annular top 21 of the collection lid with its outer edge extension 24 is rounded on the inside to seat flushly upon the upwardly facing rounded mating shoulder 12 of the lip 11 of the specimen cup in order to insure a desirable degree of water-tightness.

Figure 4:
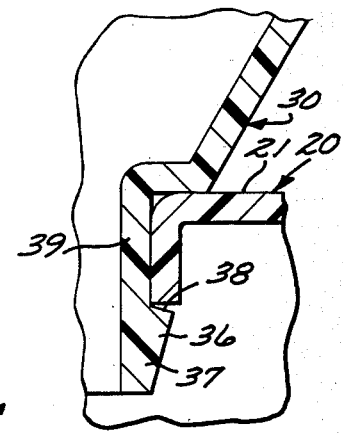
FIG. 4 is a greatly enlarged fragmentary view of area 4 indicated in FIG. 3.
Figure 5:
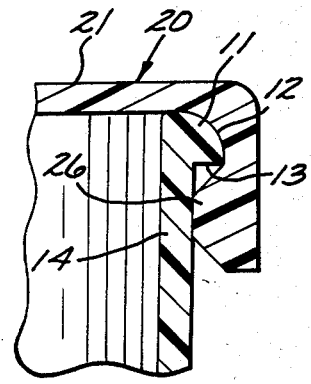
FIG. 5 is a greatly enlarged fragmentary view of area 5 indicated in FIG. 3.

The collection funnel 30 has, at the spout end, a funnel collar 34 which fits into the sleeve formed by the inner downwardly projecting cylindrical edge extension 22 of the collection lid 20. At the lower edge of the funnel collar 34 there are preferably four regularly circumferentially spaced outwardly projecting chordal rib segments 36 capable of engaging the cylindrical extension 22 of the lid 20 from underneath. As best seen in FIGS. 4 and 8, unlike the chordal rib segments 26 on the outer edge extension 24 of the collection lid 20, these rib segments 36 have upper 38 and lower 37 faces of unequal chamfer. The downwardly facing entry ramps 37 of these rib segments are acutely chamfered, to preferably approximately 15° from the vertical, so that the task of locking the funnel 30 into the collection lid 20 requires little force. The upwardly facing locking shoulders 38 of the rib segments 26, on the other hand, are only slightly chamfered off the horizontal (preferably approximately 15°). This rather severe shoulder makes disengagement of the funnel 30 from the collection lid 20 extremely difficult. As the chordal rib segments 36 of the funnel collar 34 latch past the inner edge extension 22 of the collection lid 20, the annular base 33 of the funnel 30 seats above the top 21 of the collection lid 20 clamping the lid 20 between the base 33 of the funnel 30 and the upwardly facing locking shoulders 38 of the chordal rib segments 36. The cylindrical flanking wall 39 of the funnel collar 34 lies flush against the inner face of the inner cylindrical edge extension 22 of the collection lid 20 providing a high degree of axial stability for the funnel in relation to the specimen cup. At this point the funnel and collection lid have effectively become one unit. After collection of the urine specimen, funnel 30 and lid 20 are jointly detachable as a unit from the specimen cup 10 by exerting an upward force, preferably skewed, on either the funnel 30 or the lid 20 since the connection between specimen cup 10 and collection lid 20 is more readily broken than that between collection lid 20 and funnel 30.

Given the necessity of mass production by a plant and quantity storage by a urologist or associated laboratory it is advantageous that the funnel 30 and collection lid 20 be molded separately since this makes all of the individual pieces of the current invention stackable and hence storage-efficient.

The cross-sectional area of the interior of funnel 30 expands upwardly from the circular perimeter of the funnel base 33 uniformly along two orthogonally related vertical planes of symmetry to an ovoid mouth 32. FIG. 1 shows the funnel mouth 32 to have a generally oblong shape with parallel sides and rounded, semicircular ends. The parallel sides of the funnel mouth allow it to be held easily between the user's legs during collection of a specimen. To further facilitate specimen collection, the rounded ends of the funnel mouth 32 extended upward to form a saddle shape. This shape is illustrated in FIGS. 1, 3 and 6. A vertical section taken along the lengthwise plane of symmetry (FIG. 3) reveals a uniformly concave curvature from one end to the other, while a vertical section taken along the orthogonally related plane of symmetry, or width (FIG. 6), reveals a uniformly convex curvature of the funnel mouth from side to side.

This configuration is especially accommodating for specimen collection from female subjects since urination in females lends itself to less directional control than in males. The saddle shape of the funnel mouth compensates for this difficulty by following the natural contours of the perineum allowing the funnel to be placed closely to the subject's body. The annular shape of the collection lid 20 also greatly reduces any splashing of the specimen onto the user when between the legs.

After the specimen has been collected and the collection lid 20 and funnel 30 have been removed in the manner described above, the specimen is ready to be stored until urinalysis is convenient. The specimen is retained in the specimen cup 10 and a storage lid 40 is snapped into place over the mouth of the cup. This defines the storage state of the system (FIG. 2).

The storage lid 40 has a solid circular top 42 with an annular flange 44 projecting downward from its edge. The flange 44 has an inwardly projecting full annular ridge 45 capable of interlocking with the annular lip 11 of the specimen cup 10 (FIGS. 10 and 11). As contrasted to the circumferentially spaced chordal rib segments 36 of the collection lid 20, the full annular ridge 45 of the storage lid 40 provides a positive water-tight seal to the specimen cup 10. The ridge 45 is chamfered below and above forming respectively, an entry ramp 47 and severe locking shoulder 48 (similar to the rib segments 36 protruding outward from the funnel collar, but fully annular instead of segmented). Between the upper and lower 47 chamfers of the annular ridge there is a cylindrically faced flanking 46 that presses flushly against the cylindrical mouth segment 14 of the specimen cup 10. The approximately 90° join of the flange 44 with the top 42 of the storage lid 40 structurally enhances the flexibility inherent in the material of the storage lid 40, providing a water-tight seal between specimen cup 10 and storage lid 40. Below the annular ridge 45 of the flange 44 there is a flange extension 49 that flares slightly outward from the cup mouth section 14. When the specimen is to be made available for urinalysis the storage lid 40 may be removed by flexing this flange extension 49 with an outward force exerted by thumb or fingers, or by a suitable tool.

The entire system is preferably to be molded of an inexpensive, generally rigid plastic material which has sufficient resiliency to enable the engagement and disengagement of the various parts, such as polyethylene. This renders the entire system disposable and makes it possible to avoid the danger of improper sterilization of a reusable urine collection device.

It is important that the material be of such a resilient character as to clearly differentiate the connections between specimen cup 10 and collection lid 20, collection lid 20 and funnel 30, and specimen cup 10 and storage lid 40. The full annular ridge 45 of the storage lid 40 when coupled with the lip 11 of the specimen cup 10 must provide a seal that makes it possible to conveniently transport and store a specimen for urinalysis. This full annular ridge contrasts with the interrupted chordal rib segments 26 and 36 of both the collection lid 20 and funnel collar 34 respectively. As the collection state of the system is short-lived it is desirable that the connection between specimen cup 10 and collection lid 20 allow for the easy disengagement of those two parts and hence the replacement of the collection lid 20 by the storage lid 40. No true seals are required in the collection state of the system. The severe shoulders 38 of the rib segments 36 on the funnel collar 34 do, however, interlock with the collection lid 20 strongly enough to allow the funnel 30 and collection lid 20 to remain a unit while being removed from the specimen cup 10 and subsequently thrown away. These different seals are devised, in conjunction with the other features mentioned above, to facilitate use of the system away from the laboratory or without supervision and to make specimen collection as simple and efficient as possible.

While the invention has been described with reference to presently preferred embodiments, it is to be understood that various modifications or alterations may be made by those skilled in the art without departing from the scope and spirit of the invention as set forth in the appended claims.

I claim:

1. A urine specimen collecting system which comprises:
    a collection cup having peripheral lip means proximate its top;
    collection funnel means having first peripheral connection means thereon releaseably connectable with said lip means at a first connection with the inside of said funnel means in communication with the inside of said cup means for collection of a urine specimen through said funnel means into said cup;
    a storage lid having second peripheral connection means thereon releasably connectable with said lip means at a second connection so as to cover said cup;
    said funnel means comprising a funnel and a collection lid;
    said funnel being connectable to said collection lid and said first connection means being on said collection lid;
    the connection between said funnel and said collection lid having a smaller diameter than said peripheral lip means of said cup;
    the connection between said funnel and said collection lid being more secure than said first connection, whereby said collection funnel means is adapted to be disengaged as a unit including said funnel and said collection lid from said collection cup.

2. A urine specimen collection system as defined in claim 1 wherein said collection cup, said funnel and said collection lid may be assembled into the collection mode of said urine specimen collecting system;
    said connection between said funnel and said collection lid being substantially irreversible such that said collection funnel means may be readily removed as a unit from said collection cup after said collection of said urine specimen.

3. A urine specimen collection system as defined in claim 1 wherein said lip means is substantially uninterrupted.

4. A urine specimen collection system as defined in claim 1 wherein said first connection means comprises a plurality of spaced ribs adapted to be snapped over said lip means.

5. A urine specimen collection system as defined in claim 1 wherein said second connection means comprises a substantially uninterrupted flange adapted to be snapped over said lip means.

6. A urine specimen collection system as defined in claim 1 wherein said connection between said funnel and said collection lid comprises funnel connection means proximate the spout end of said funnel adapted to be snapped into the center of said collection lid.

7. A urine specimen collection system as defined in claim 6 wherein said flange means proximate said spout comprises spaced peripheral ribs adapted to be snapped into the center of said collection lid.

8. A urine specimen collection system as defined in claim 2 wherein said first connection means has first flange shoulder means thereon engageable with said lip, and said connection between said funnel and said collection lid comprises second flange shoulder means on said funnel engageable with said collection lid;
said second flange shoulder means being more abrupt for more secure engagement than said first shoulder means.

9. A urine collection system as defined in claim 1, wherein said second connection has a substantially water-tight seal.

10. A urine collection system as defined in claim 1, wherein said second connection has a better liquid seal than said first connection.

11. A urine collection system as defined in claim 1, wherein said lip means is substantially uninterrupted;
said first connection means comprising a plurality of spaced ribs adapted to be snapped over said lip means; and
said second connection means comprising a substantially uninterrupted flange adapted to be snapped over said lip means after said first connection has been disengaged and said funnel means removed from said cup.

* * * * *